United States Patent
Morita et al.

[11] Patent Number: 6,057,386
[45] Date of Patent: May 2, 2000

[54] SILICONE OIL EMULSION, COMPOSITION AND METHOD OF MANUFACTURE

[75] Inventors: Yoshitsugu Morita; Kazuo Kobayashi; Ryuji Tachibana, all of Chiba Prefecture, Japan

[73] Assignee: Dow Corning Toray Silicone Co. Ltd., Tokyo, Japan

[21] Appl. No.: 09/263,564

[22] Filed: Mar. 8, 1999

[30] Foreign Application Priority Data

Jun. 10, 1998 [JP] Japan .................................. 10-178116

[51] Int. Cl.⁷ .................... C08K 9/06; C08K 3/34
[52] U.S. Cl. ............................... 523/212; 524/442
[58] Field of Search ............... 523/212; 524/442

[56] References Cited

U.S. PATENT DOCUMENTS

| | | | |
|---|---|---|---|
| 3,685,163 | 8/1972 | Olt | 34/5 |
| 4,962,165 | 10/1990 | Bortnick et al. | 525/479 |
| 4,980,167 | 12/1990 | Harashima et al. | 424/401 |
| 4,987,169 | 1/1991 | Kuwata et al. | 524/267 |
| 5,154,849 | 10/1992 | Visscher et al. | 252/174.15 |
| 5,628,989 | 5/1997 | Harashima et al. | 424/65 |
| 5,708,057 | 1/1998 | Morita et al. | 523/402 |
| 5,760,109 | 6/1998 | Inokuchi et al. | 523/414 |
| 5,849,310 | 12/1998 | Trinh et al. | 424/401 |
| 5,854,336 | 12/1998 | Divone, Sr. et al. | 524/588 |

FOREIGN PATENT DOCUMENTS 829253  3/1998  European Pat. Off. ......... A61K 7/00

*Primary Examiner*—Kriellion Sanders
*Attorney, Agent, or Firm*—James L. De Casare

[57] ABSTRACT

A silicone emulsion contains cross-linked silicone particles in silicone oil drops dispersed in water. A method for the preparation of the emulsion, and a method for the preparation of a silicone composition with cross-linked silicone particles uniformly dispersed in a silicone oil, is also provided.

6 Claims, No Drawings

SILICONE OIL EMULSION, COMPOSITION AND METHOD OF MANUFACTURE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to a silicone oil emulsion, a method of manufacturing thereof, a silicone composition, and a method for manufacturing a silicone composition.

BACKGROUND OF THE INVENTION

The present invention relates to a silicone oil emulsion, a method of manufacturing of the aforementioned emulsion, and a method for the preparation of a silicone composition. More specifically, the invention concerns a silicone oil emulsion that contains cross-linked silicone particles in silicone oil drops which are dispersed in water; a method of manufacturing the aforementioned silicone oil emulsion; and a method for the preparation of a silicone composition comprising cross-linked silicone particles uniformly dispersed in a silicone oil.

A method of manufacturing cross-linked silicone particles which contain non-cross-linkable silicone oil is known. The particles are prepared by dispersing a cross-linkable silicone composition that contains the non-cross-linkable silicone oil in water and causing a cross-linking reaction, i.e. Japanese Laid-Open Patent Application Kokai Sho 01-81856 and Hei 2-243612 (U.S. Pat. No. 4,980,167). This method, however, does not allow the obtaining of a silicone oil emulsion which would contain cross-linked silicone particles in silicone oil drops dispersed in water.

A method for the preparation of a silicone oil emulsion which contains cross-linked silicone particles dispersed in it and drops of silicone oil in water is also known. This method comprises combining cross-linked silicone particles with a silicone oil emulsion containing silicone oil drops dispersed in water, i.e. Japanese Laid-Open Patent Application Kokai Hei 3-271211 and Hei 9-53047 (U.S. Pat. No. 5,760,109). In this method, however, silicone oil drops and cross-linked silicone particles are dispersed in water independently, and therefore this method is not suitable for the preparation of silicone oil emulsions that would contain cross-linked silicone particles in the silicone oil drops.

Furthermore, known in the art are silicone compositions comprising cross-linked silicone particles dispersed in silicone oil, i.e., Japanese Laid-Open Patent Applications Kokai Sho 63-152308, Hei 1-165509, Hei 1-207354, Hei 2-43263 (U.S. Pat. No. 4,987,169), Hei 6-502646 (U.S. Pat. No. 5,1548,49) and Hei 7-330537. The silicone compositions can be prepared by mixing a silicone oil with cross-linked silicone particles, or by treating the product of cross-linking of a cross-linkable silicone composition, which contains non-cross-linkable silicone oil, with shearing forces, i.e., Japanese Laid-Open Patent Application Hei 2-43263. However, in silicone compositions prepared by the above methods, cross-linked silicone particles are dispersed in silicone oil nonuniformly, and therefore they cannot demonstrate their specific properties sufficiently.

BRIEF SUMMARY OF THE INVENTION

It is an object of the present invention to provide a silicone oil emulsion that contains cross-linked silicone particles in silicone drops which are dispersed in water; a method of manufacturing the silicone oil emulsion; and a method for the preparation of a silicone composition comprising cross-linked silicone particles uniformly dispersed in a silicone oil.

A silicone oil emulsion of the present invention is characterized by cross-linked silicone particles which have an average particle diameter of 0.1 to 100 μm which are contained in silicone oil drops having an average diameter of 0.5 to 500 μm, and which are dispersed in water, provided that the diameter of the cross-linked silicone particles is smaller than the diameter of the silicone oil drops.

Furthermore, the method of the invention for manufacturing a silicone oil emulsion is characterized by a cross-linking reaction carried out by dispersing in water a cross-linkable silicone composition, that contains a non-cross-linkable silicone oil. The contents of the non-cross-linkable silicone oil exceed the contents of the non-cross-linkable silicone oil in the product of cross-linking of the cross-linkable silicon composition.

The method for the preparation of the silicone composition of the present invention is characterized by removing water from a silicone oil emulsion which contains cross-linked silicone particles having an average particle diameter of 0.1 to 100 μm, the particles being contained in silicone oil drops having an average diameter of 0.5 to 500 μm and dispersed in water, provided the diameter of the cross-linked silicone particles is smaller than the diameter of the silicone oil drops.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The following is a more detailed description of a silicone oil emulsion of the present invention.

An emulsion of the present invention contains cross-linked silicone particles in silicone oil drops which are dispersed in water. The cross-linked silicone particles contained in the emulsion of the present invention are obtained by cross-linking a cross-linkable composition. This composition can be prepared by causing a hydrosylilation cross-linking reaction, a condensation cross-linking reaction, an organic-peroxide type cross-linking reaction, or a high-energy ray cross-linking reaction. The most preferable is the hydrosylilation cross-linking reaction or the condensation cross-linking reaction.

There are no special limitations with regard to the types of silicone oil used for the formation of the silicone oil drops. The silicone oil may have a completely linear, partially-branched linear, cyclic, or a branched-chain molecular structure. The most preferable is a linear or a cyclic molecular structure. It is preferred that the silicone oil not participate in the cross-linking reaction during formation of the cross-linked silicone particles. In other words, when the cross-linked silicone particles are formed by a hydrosylilation cross-linking reaction, it should be a silicone oil which does not contain in its molecules alkenyl groups and silicon-bonded hydrogen atoms. For example the silicone oil can be a dimethylpolysiloxane having both molecular terminals capped with trimethylsiloxy groups, a methylphenylpolysiloxane having both molecular terminals capped with trimethylsiloxy groups, a copolymer of methylphenylsiloxane and dimethylsiloxane having both molecular terminals capped with trimethylsiloxy groups, a copolymer of methyl (3,3,3-trifluoropropyl) siloxane and dimethylsiloxane having both molecular terminals capped with trimethylsiloxy groups, a cyclic dimethylsiloxane, or a cyclic methylphenylsiloxane. When the cross-linked silicone particles are formed by a condensation cross-linking reaction, it is preferred that the oil be a compound which does not contain in its molecules silanole groups, silicon-bonded hydrogen atoms, and silicon-bonded hydrolyzable groups. For example, the silicone oil can be an oil similar to those mentioned above, i.e., a dimethylpolysiloxane having both molecular terminals capped with dimethylvinylsiloxy groups, a copolymer of methylvinylsiloxane and dimethylsiloxane having both molecular terminals capped with dimethylvinylsiloxy groups, a methylvinylpolysiloxane having both molecular terminals capped with trimethylsiloxy groups, or a cyclic methylvinylsiloxane. It is preferred that the silicone oil have a viscosity of 1 to 100,000,000 mPa.s, preferably 2 to 10,000,000 mPa.s, at 25° C.

It is preferred that the average diameter of silicone oil drops in the emulsion of the present invention be within a range of 0.1 to 500 μm, preferably within a range of 0.5 to 200 μm. This is because an emulsion with an average diameter of drops beyond the limits of this range will have low stability.

It is preferred that the average diameter of cross-linked silicone particles in the emulsion of the present invention be within a range of 0.1 to 100 μm, preferably within a range of 0.5 to 50 μm. This is because an emulsion with an average diameter of particles beyond the limits of this range will have low stability. In the emulsion of the present invention, the diameter of the cross-linked silicone particles should be smaller than the diameter of the silicone oil drops. The cross-linked silicone particles may have a spherical, thread-like, flat, or irregular shape. A spherical shape is preferable.

The emulsion of the present invention can be used as a starting material for the preparation of cosmetic substances. By removing water from the emulsion, it is possible to obtain a liquid, cream-like, paste-like, or a grease-like silicone composition having cross-linked silicone particles uniformly dispersed in silicone oil.

The following is a description of a method for manufacturing the silicone oil emulsion of the present invention. A cross-linkable silicone composition suitable for the manufacturing method of the present invention may be a hydrosylilation cross-linking reaction type, a condensation cross-linking reaction type, an organic-peroxide cross-linking reaction type, or a cross-linking reaction performed by irradiating the composition with high-energy rays. The most preferable is a hydrosylilation cross-linking reaction or a condensation cross-linking reaction.

The hydrosylilation cross-linking reaction type silicone composition comprises an organopolysiloxane having in its molecule at least two alkenyl groups, an organopolysiloxane having in its molecule at least two silicone-bonded hydrogen atoms, and a catalyst for the hydrosylilation reaction.

Alkenyl groups in the first-mentioned organopolysiloxane may be represented by vinyl groups, allyl groups, butenyl groups, pentenyl groups, and hexenyl groups. The most preferable are vinyl groups. Groups other than alkenyl groups that can be contained in the first-mentioned organopolysiloxane are monovalent hydrocarbon groups such as methyl groups, ethyl groups, propyl groups, butyl groups, or similar alkyl groups; cyclopentyl groups, cyclohexyl groups, or similar cycloalkyl groups; phenyl groups, tolyl groups, xylyl groups, or similar aryl groups; benzyl groups, phenethyl groups, 3-phenylpropyl groups, or similar aralkyl groups; 3-chloropropyl groups, 3,3,3-trifluoropropyl groups, or similar halogenated hydrocarbon groups. The organopolysiloxane groups may have a linear, cyclic, branched, or partially-branched linear molecular structure. In order to form elastomer-like cross-linked silicone particles, the linear and partially-branched linear structures are preferable. Although there are no special limitations with regard to the viscosity of the organopolysiloxane, it should be one that does not limit the dispersing of the cross-linkable silicone composition in water. It is preferred that at 25° C., the viscosity be within a range of 20 to 100,000 mPa.s, preferably between 20 and 10,000 mPa.s.

Examples of groups other than hydrogen atoms in the second-mentioned organopolysiloxane are the same as the aforementioned monovalent hydrocarbon groups. The second-mentioned organopolysiloxane may have a linear, cyclic, branched, or partially-branched linear structure. Although there are no special limitations with regard to viscosity of this organopolysiloxane, it should not limit dispersing of the cross-linkable silicone composition in water. It is preferred that at 25° C. the viscosity be within a range of 1 to 10,000 mPa.s. It is preferred that this organopolysiloxane be used in the cross-linkable silicone composition in an amount sufficient for curing the composition, preferably in an amount of 0.3 to 200 parts by weight per 100 parts by weight of the first-mentioned organopolysiloxane.

The hydrosylilation reaction catalyst contained in the cross-linkable silicone composition of the present invention is a catalyst for acceleration of cross-linking of the composition. Preferably, it should be a platinum catalyst such as chloroplatinic acid, an alcoholic solution of chloroplatinic acid, an olefin complex of platinum, an alkenylsiloxane complex of platinum, platinum black, or silica on a platinum carrier. A cross-linkable silicone composition that contains the hydrosylilation catalyst in water can be prepared by dispersing in water the cross-linkable silicone composition which has been premixed with the hydrosylilation catalyst, or the catalyst can be added to water after dispersing it in the catalyst-free cross-linkable silicone composition. It is preferred to use an aqueous dispersion containing the hydrosylilation catalyst with an average particle diameter not exceeding 1 μm. It is preferred that the hydrosylilation catalyst be used in the cross-linkable composition in an amount sufficient for accelerating the cross-linking of the cross-linkable composition. For example, when a platinum-system catalyst is used as a hydrosylilation catalyst, it should be used in an amount of $1\times10^{-7}$ to $1\times10^{-3}$ parts by weight of platinum metal per 100 parts by weight of the organopolysiloxane.

A condensation cross-linking reaction type silicone composition may comprise, at least, an organopolysiloxane which contains a hydrolyzable group such as an aminoxy group, acetoxy group, oxime group, alkoxy group or a hydroxyl group bonded to at least two silicon atoms in one molecule, or similar groups; a silane-type cross-linking agent having a hydrolyzable group such as an aminoxy group, acetoxy group, oxime group, alkoxy group bonded to at least three silicon atoms in one molecule or similar groups; and a condensation reaction catalyst such as an organic titanium compound, an organic tin compound, or similar compounds.

Alkoxy groups contained in the organopolysiloxane can be represented by methoxy groups, ethoxy groups, and methoxyethoxy groups. Oxime groups contained in the organopolysiloxane can be represented by dimethylketoxime groups and methylethylketoxime groups. Other groups that can be contained in the organopolysiloxane can be monovalent hydrocarbon groups such as methyl groups, ethyl groups, propyl groups, butyl groups, or similar alkyl groups; cyclopentyl groups, cyclohexyl groups, or similar cycloalkyl groups; vinyl groups, allyl groups, butenyl groups, pentenyl groups, hexenyl groups; phenyl groups, tolyl groups, xylyl groups, or similar aryl groups; benzyl groups, phenethyl groups, 3-phenylpropyl groups, or similar aralkyl groups; 3-chloropropyl groups, 3,3,3-trifluoropropyl groups, or similar halogenated hydrocarbon groups. The organopolysiloxane may have a linear, cyclic, branched, or a partially-branched linear molecular structure. The linear or partially-branched linear molecular structure is preferable for the formation of elastomer-like cross-linked silicone particles. Although there are no special limitations with regard to the viscosity of the organopolysiloxane, it should not limit the dispersing of the cross-linkable silicone composition in water. It is preferred that at 25° C. the viscosity be within a range of 20 to 100,000 mPa.s, preferably between 20 and 10,000 mPa.s.

Oxime groups and alkoxy groups contained in the silane-type cross-linking agent may be the same as those exemplified above. The silane-type cross-linking agent can be represented by methyltrimethoxysilane, vinyltrimethoxysilane, methyltrioximesilane, and vinyltrioximesilane. It is recommended that the silane-type cross-linking agent be used in the cross-linkable silicone composition in an amount sufficient for curing the composition, preferably in an amount of 0.3 to 200 parts by weight per 100 parts by weight of the organopolysiloxane.

The condensation reaction catalyst is an organic tin compound, or organic titanium compound, and is intended for accelerating the reaction of cross-linking of the cross-linkable silicone compound. Such a catalyst can be represented by dibutyltin dilaurate, dibutyltin diacetate, tin octenate, dibutyltin dioctate, tin laurate, tetrabutyl titanate, tetrapropyl titanate, and dibutoxy bis(ethylacetoacetate). It is preferred that the condensation reaction catalyst be used in the cross-linkable silicone composition in an amount sufficient for cross-linking of the composition, preferably in an amount of 0.01 to 5 parts by weight, more preferably 0.05 to 2 parts by weight per 100 parts by weight of the organopolysiloxane.

A filler can be added to the cross-linkable silicone composition either for adjusting its flowability, or for improving the mechanical strength of the obtained cross-linked silicone particles. Examples of such a filler are precipitated silica, fumed silica, baked silica, fumed titanium oxide, or a similar reinforcing filler; crushed quartz, diatomaceous earth, aluminosilicic acid, ferrous oxide, zinc oxide, calcium oxide, or a similar non-reinforcing filler. The surfaces of these fillers can be treated with hexamethylsilazane, trimethylchlorosilane, polydimethylsiloxane, polymethylhydridosiloxane, or similar organosilicon compounds.

By means of a cross-linking reaction, the cross-linkable silicone composition can be converted to a rubber-like, gel-like or a similar elastomeric cross-linked substance.

The non-cross-linkable silicone oil contained in the cross-linkable silicone composition is one that does not participate in the cross-linking of the composition. It may have a linear, partially-branched linear, cyclic, or a branched molecular structure. Among these, linear and cyclic structures are preferable. In the case where the composition is of a hydrosylilation cross-linking reaction type, it is preferred that the non-cross-linkable silicone oil does not contain alkenyl groups or silicon-bonded hydrogen atoms in its molecule. Examples of such oils are a dimethylpolysiloxane having both of its molecular terminals capped with trimethylsiloxy groups, a methylphenylpolysiloxane having both of its molecular terminals capped with trimethylsiloxy groups, a copolymer of methylphenylsiloxane and dimethylsiloxane having trimethylsiloxy groups on both molecular terminals, a copolymer of methyl (3,3,3-trifluoropropyl) siloxane and dimethyl siloxane having trimethylsiloxy groups on both molecular terminals, a cyclic dimethyl siloxane, and a cyclic methylphenylsiloxane. When the composition is of a condensation cross-linking type, it is preferred that the oil be free of silanol groups, silicon-bonded hydrogen atoms, and silicon-bonded hydrolyzable groups. The oils can be the same silicone oils as those listed above, or dimethylpolysiloxanes having both molecular terminals capped with dimethylvinylsiloxy groups, a copolymer of methylvinylsiloxane and dimethylsiloxane having dimethylvinylsiloxy groups on both molecular terminals, a methylvinylpolysiloxane having trimethylsiloxy groups at both molecular terminals, or a cyclic methylvinylsiloxane. It is preferred that the non-cross-linkable silicone oil have at 25° C. a viscosity within a range of 1 to 100,000,000 mPa.s, preferably between 2 and 10,000,000 mPa.s.

The non-cross-linkable silicone oil contained in the cross-linkable compound should be used in an amount sufficient for maintaining the non-cross-linkable silicone oil in the product resulting from cross-linking of the cross-linkable silicone composition. More specifically, it should be used in excess of the quantity of the non-cross-linkable oil that can be held by the product of cross-linking. The amount that can be held is different from a mere combination of the cross-linkable silicone compositions and the non-cross-linkable silicone oil. In general, however, a non-cross-linkable silicone oil should be used in an amount within a range of 200 to 5,000 parts by weight, preferably 250 to 2,000 parts by weight per 100 parts by weight of the cross-linkable silicone composition.

The method of the present invention may consist of dispersing a cross-linkable silicone composition that contains the non-cross-linkable silicone oil in water, and then conducting a cross-linking reaction. Dispersing the cross-linkable silicone composition in water can be carried out with the use of a homomixer, paddle mixer, Henschel mixer, homodisperser, colloid mixer, propeller-type stirrer, homodisperser, homogenizer, in-line type continuous emulsifier, ultrasound emulsifier, vacuum kneader, or other device for dispersing compositions in water.

There are no special limitations with regard to the amount of water used in the method. It is preferred, however, that water be used in an amount of 5 to 99 wt. %, preferably 10 to 80 wt. % based upon the total weight of the emulsion.

If it is desired to improve the stability of the cross-linkable silicone composition in water or to ensure dispersion, the composition can be combined with a nonionic surface-active agent, a cationic surface-active agent, or an anionic surface-active agent. The most preferable surface-active agent is a nonionic surface-active agent. It is recommended that the surface-active agent be used in an amount of 0.1 to 20 parts by weight, preferably 0.5 to 10 parts by weight per 100 parts by weight of the cross-linkable silicone composition that contains the non-cross-linkable silicone oil.

The emulsion of the cross-linkable silicone composition is then either heated, maintained at room temperature, or irradiated with high-energy rays, whereby a cross-linking reaction is caused in the cross-linkable silicone composition dispersed in water.

It is most preferred that silicone oil drops dispersed in water have an average diameter within a range of 0.1 to 500 $\mu$m, preferably 0.5 to 200 $\mu$m. If an average diameter of drops is below the lower limit or exceeds the upper limit, the emulsion will tend to lose its stability.

It is also most preferred that the cross-linked silicone particles contained in the silicone oil drops have an average diameter within a range of 0.1 to 100 $\mu$m, preferably 0.5 to 50 $\mu$m. This is because, if the diameter of the cross-linked silicone particles is below the lower limit or above the upper limit, the emulsion will tend to lose its stability. It should be apparent that, in accordance with the method of the invention, the diameter of the cross-linked silicone particles should be smaller than the diameter of the silicone-oil drops. The cross-linked silicone particles may have a spherical, needle-like, flat, or irregular shape. A spherical shape is preferable.

The following is a more detailed description of the method used for the preparation of the silicone composition of the present invention. The method consists of removal of water from the silicone oil emulsion that contains cross-linked silicone particles in silicone oil drops dispersed in water. The cross-linked silicone particles contained in the silicone oil emulsion are produced by cross-linking the cross-linkable silicone composition. Such a cross-linkable silicone composition may be a hydrosilylation cross-linking reaction type, a condensation cross-linking reaction type, an organic peroxide cross-linking reaction type, or a high-energy ray cross-linking reaction type. The hydrosilylation cross-linking reaction type or condensation cross-linking reaction type silicone composition is preferable.

There are no special limitations with regard to the type of a silicone oil which forms silicone oil drops in the silicone oil emulsion used in the preparation method of the present invention. The silicone oil may have a linear, cyclic, branched, or other molecular structure. The linear or cyclic molecular structure is preferable. It is preferred that the silicone oil does not participate in the cross-linking reaction during the formation of cross-linked silicone particles, and that in the case where the cross-linked silicone particles are formed by a hydrosylilation cross-linking reaction, the molecule of the oil does not contain alkenyl groups and silicon-bonded hydrogen atoms. For example, the oil can be a dimethylpolysiloxane having both molecular terminals capped with trimethylsiloxy groups, a methylphenylpolysiloxane having both molecular terminals capped with trimethylsiloxy groups, a copolymer of methylphenylsiloxane and dimethylsiloxane having both molecular terminals capped with trimethylsiloxy groups, a copolymer of methyl (3,3,3-trifluoropropyl) siloxane and dimethylsiloxane having both molecular terminals capped with trimethylsiloxy groups, a cyclic dimethylsiloxane, or a cyclic methylphenylsiloxane. When the cross-linked silicone particles are formed by means of a condensation cross-linking reaction, it is preferred that the oil be represented by compounds which do not contain in their molecules silanol groups, silicon-bonded hydrogen atoms, and silicon-bonded hydrolyzable groups such as silicone oils similar to those mentioned above, or a dimethylpolysiloxane having both molecular terminals capped with dimethylvinylsiloxy groups, a copolymer of methylvinylsiloxane and dimethylsiloxane having both molecular terminals capped with dimethylvinylsiloxy groups, a methylvinylpolysiloxane having both molecular terminals capped with trimethylsiloxy groups, or a cyclic methylvinylsiloxane. It is preferred that the silicone oil have at 25° C. a viscosity of 1 to 100,000,000 mPa.s, preferably 2 to 10,000,000 mPa.s.

The average diameter of silicone oil drops in the emulsion of the present invention should be within a range of 0.1 to 500 $\mu$m, preferably within a range of 0.5 to 200 $\mu$m. This is because the emulsion with an average diameter of drops beyond these limits will have low stability.

The average diameter of cross-linked silicone particles in the silicone oil emulsion of the present invention should be within a range of 0.1 to 100 $\mu$m, preferably within a range of 0.5 to 50 $\mu$m. This is because an emulsion with an average diameter of particles less than the lower limit or higher than the upper limit will have low stability. It should be apparent that in the emulsion of the present invention, the diameter of the cross-linked silicone particles should be smaller than the diameter of the silicone oil drops. The cross-linked silicone particles may have a spherical, thread-like, flat, or irregular shape. The spherical shape is preferable.

Although there are no special limitations with regard to the method for the preparation of the silicone oil emulsion, the method described above is preferable. In this method, water can be removed from the emulsion by air drying, hot-air drying, vacuum drying, or heating. A silicone composition obtained by this method comprises a dispersion of cross-linked silicone particles in silicone oil. This composition can be prepared in a liquid, cream-like, paste-like, or a grease-like form. The composition can be used as a lubricating agent or a cosmetic substance.

EXAMPLES

The silicone oil emulsions of the invention, methods of their preparation, and methods for the preparation of the silicone compositions of the invention will now be considered in more detail with reference to the following practical examples. In these examples, all values of viscosity were measured at 25° C. The following procedures were used for determining an average diameter of particles in the silicone oil emulsion, an average diameter of cross-linked silicone particles, and various characteristics of the silicone composition.

Average Diameter of Particles in the Silicone Oil Emulsion

The diameter of silicone oil emulsion particles was measured with the use of a laser-diffraction type particle distribution measurement instrument of Horiba Seisakusho Co., model LA-500. The obtained median diameter (a particle diameter corresponding to 50% of the accumulated distribution) was defined as an average particle diameter.

Stability of the Silicone Oil Emulsion 180 mL of the silicone oil emulsion was sealed in a 225 mL glass bottle 105 mm-deep, 50 mm-diameter bottle and kept for 1 week at room temperature. The thickness of a layer of water which had been separated from the silicone oil emulsion was then measured.

Dispersibility of Cross-Linked Silicone Particles

A silicone oil emulsion was dried in air on a glass plate, and then the shape, aggregation, and distribution of cross-linked silicone particles were observed under a stereoscopic microscope. Structures with a dispersion of primary particles were designated by a symbol "◯", aggregated particles with the size of about several hundred microns and primary particles exceeding in size 500 μm were designated by a symbol "x", and the particles having intermediate dimensions between the aforementioned categories were designated by a symbol "Δ".

Average Diameter of Cross-Linked Silicone Particles

The silicone oil emulsion was dried in air on a glass plate, and then a sample was prepared under a stereoscopic microscope by accumulating the cross-linked particles. The collected sample was then observed under an electronic microscope, and an average particle diameter was determined based on 10 particles.

Viscous-Elastic Properties of the Silicone Composition

A storage elasticity coefficient G' ($\times 10^3$ dyne/cm$^2$), loss elasticity coefficient G" ($\times 10$ dyne/cm$^2$), and loss tan δ were measured by means of an ARES viscosimeter of Reometric Scientific Co., Inc. Measurements were carried out under the following conditions: room temperature; 25 mm parallel plates; 0.5 to 0.6 mm gap; 10% strain; 0.1 to 50 rad/s oscillation frequency.

Practical Example 1

A cross-linkable silicone composition was prepared by mixing the following components: 18.8 parts by weight of a dimethylpolysiloxane having 400 mPa.s viscosity and dimethylvinylsiloxy groups on both molecular terminals; 1.2 parts by weight of a 30 mPa.s viscosity copolymer of methylhydridosiloxane and dimethylsiloxane having trimethylsiloxy groups on both molecular terminals and 0.5 wt. % content of silicon-bonded hydrogen; and 80 parts by weight of a 100 mPa.s viscosity dimethylpolysiloxane having trimethylsiloxy groups on both molecular terminals. The obtained cross-linkable silicone composition was then combined with 53 parts by weight of a 3 wt. % aqueous solution of polyoxyethylene nonylphenylether (HLB=13.1). After emulsification, 50 parts by weight of pure water were added to the mixture. As a result, an aqueous emulsion of a cross-linkable silicone composition was prepared.

A platinum catalyst comprising a complex of platinum and 1,1-divinyl-1,1,3,3-tetramethoxydisiloxane as its main component with an average diameter of the platinum catalyst particles equal to 0.05 μm and concentration of metallic platinum of 0.05 wt. % was added to the aforementioned aqueous emulsion of the cross-linkable silicone composition, and the components were uniformly mixed so that the contents of the metallic platinum in weight units became equal to 20 ppm. As a result, an aqueous emulsion of a cross-linkable silicone composition was obtained.

The obtained emulsion was kept intact at room temperature for one day, and then the cross-linkable silicone composition was subjected to a hydrosylilation reaction, whereby there was prepared a silicone oil emulsion having cross-linked silicone particles in drops of silicone oil dispersed in water.

The emulsion was then transferred to a 5 cm diameter aluminum plate, and water was removed from the emulsion by drying in air, while maintaining it in air draft for 3 days. As a result, a silicone composition consisting of a silicone oil and silicone particles was prepared. This silicone composition had a cream-like form. Observation of the composition under a stereoscopic microscope showed that it consisted of cross-linked silicone particles dispersed in the silicone oil. The cross-linked silicone particles were spherical in shape.

Practical Example 2

An aqueous emulsion of a cross-linked silicone composition was prepared by the same method as in Practical Example 1, with the exception that 80 parts by weight of a 6 mPa.s viscosity dimethylpolysiloxane having trimethylsiloxy groups on both molecular terminals were used instead of 80 parts by weight of a 100 mPa.s viscosity dimethypolysiloxane having trimethylsiloxy groups on both molecular terminals used in Practical Example 1. Similar to Practical Example 1, the emulsion was subjected to a hydrosylilation reaction, whereby a silicone oil emulsion having cross-linked silicone particles in silicone oil drops dispersed in water was obtained.

A silicone composition consisting of a silicone oil and cross-linked silicone particles was prepared by removing water from the aforementioned emulsion in the same manner as in Practical Example 1. The obtained composition had a cream-like appearance. Observation of the composition under a stereoscopic microscope showed that it consisted of cross-linked silicone particles dispersed in the silicone oil. The cross-linked silicone particles were spherical in shape.

Practical Example 3

A mixture was prepared by uniformly mixing the following components: 100 parts by weight of a dimethylpolysiloxane having 1,000 mPa.s viscosity and hydroxyl groups on both molecular terminals with content of hydroxyl groups of 1.3 wt. %, 4.83 parts by weight of a 10 mPa.s viscosity methylhydridopolysiloxane having trimethylsiloxy groups on both molecular terminals with 1.5 wt. % content of silicon-bonded hydrogen; 500 parts by weight of a 1000 mPa.s viscosity dimethylpolysiloxane having trimethylsiloxy groups on both molecular terminals; and 0.75 parts by weight of dibutyltin dioctate. The composition was then combined with a mixture consisting of 5 wt. % of Tergitol TMN-6, a product of Union Carbide Co., and which is an ethyleneoxide adduct of trimethylnonanole; and 80 parts by weight of ion-exchange water. The obtained product was emulsified and then combined with 35 parts by weight of pure water. As a result, an aqueous emulsion of a cross-linkable silicone composition was prepared.

A portion of the obtained emulsion was sprayed with a spray drier with an input temperature of 300° C. and an output temperature of 100° C. A grease-like substance was accumulated on the inner walls of the drier, so it was impossible to obtain cross-linked silicone particles.

After subjecting the cross-linkable silicone composition to a condensation cross-linking reaction by keeping the aforementioned aqueous emulsion of the cross-linked silicone composition intact for 1 week at room temperature, a silicone oil emulsion containing cross-linked silicone particles in silicone oil drops dispersed in water was prepared.

A silicone composition consisting of a silicone oil and cross-linked silicone particles was prepared by removing water from the aforementioned emulsion in the same manner as in Practical Example 1. The obtained composition had a cream-like appearance. Observation of the composition under a general-purpose microscope showed that it consisted of cross-linked silicone particles uniformly dispersed in the silicone oil. The cross-linked silicone particles were spherical in shape.

Comparative Example 1

A mixture "A" was prepared by uniformly mixing the following components: 100 parts by weight of a dimethylpolysiloxane having 1,000 mPa.s viscosity and hydroxyl groups on both molecular terminals with a content of hydroxyl groups of 1.3 wt. %; 10 parts by weight of a 10 mPa.s viscosity methylhydridopolysiloxane having trimethylsiloxy groups on both molecular terminals with 1.5 wt. % content of silicon-bonded hydrogen; and 50 parts by weight of a 1000 mPa.s viscosity dimethylpolysiloxane having trimethylsiloxy groups on both molecular terminals.

A mixture "B" was prepared by uniformly mixing the following components: 100 parts by weight of a dimethylpolysiloxane having 1,000 mPa.s viscosity and hydroxyl groups on both molecular terminals with the content of hydroxyl groups of 1.3 wt. %; 50 parts by weight of a 1000 mPa.s viscosity dimethylpolysiloxane having trimethylsiloxy groups on both molecular terminals; and 1.5 parts by weight of dibutyltindioctate.

After combining mixture "A" and mixture "B" in a 1:1 ratio, the product was further combined with a mixture consisting of 5 wt. % of Tergitol TMN-6 and 1700 parts by weight of ion-exchange water. The obtained product was emulsified. After removal of water, cross-linked silicone particles were obtained with a 98% yield. The obtained particles had rubber-like properties and were of a spherical shape. However, bleeding of silicone oil derived from cross-linked silicone particles was observed.

Comparative Example 2

A cross-linkable silicone composition was prepared by mixing the following components: 44.5 parts by weight of a dimethylpolysiloxane having 5 mPa.s viscosity and vinylmethylsiloxy groups on both molecular terminals; 100 parts by weight of a 20 mPa.s viscosity methylhydridopolysiloxane with a content of silicon-bonded hydrogen atoms of 1.5 wt. %; and 758 parts by weight of a 6 mPa.s viscosity dimethylpolysiloxane having trimethylsiloxy groups on both molecular terminals and 1.5 wt. % content of silicon-bonded hydrogen; and 50 parts by weight of a 1000 mPa.s viscosity dimethylpolysiloxane having trimethylsiloxy groups on both molecular terminals. A cross-linkable silicone composition was then prepared by adding 0.5 parts by weight of a 2 wt. % isopropanol solution of chloroplatinic acid. The obtained cross-linkable silicone composition was heated to 70–80° C., stirred for 2 hours, whereby hydrosylilation cross-linking of the aforementioned cross-linkable composition was performed. A moderate silicone composition was produced. This composition was kneaded between three rollers under shearing conditions, whereby a paste-like silicone composition was prepared. Observations under a general-purpose microscope showed that the silicone particles dispersed in the silicone oil had an irregular shape, the dispersion was non-uniform, and the diameter of the cross-linked silicone particles was within a range of 100 to 500 μm.

TABLE 1

| | Type | | | | |
| | Present Invention | | | Comp. Examples | |
| Item | Pr. Ex. 1 | Pr. Ex. 2 | Pr. Ex. 3 | Comp. Ex. 1 | Comp. Ex. 2 |
|---|---|---|---|---|---|
| Average Particle Diameter (μm) in Silicone Oil Emulsion | 8 | 7 | 5 | 5 | — |
| Stability (mm) | 0 | 0 | 5 | 49 | — |
| Dispersibility of Cross-Linked Silicone Particles | ○ | ○ | Δ | X | — |
| Average Particle Diameter (μm) | 3 | 3 | 2 | 5 | 17 |

TABLE 1-continued

| | Type | | | | |
| | Present Invention | | | Comp. Examples | |
| Item | Pr. Ex. 1 | Pr. Ex. 2 | Pr. Ex. 3 | Comp. Ex. 1 | Comp. Ex. 2 |
|---|---|---|---|---|---|
| Silicone Composition | | | | | |
| G' 1 rad/s | 9.7 | 15 | 0.15 | — | 5.0 |
| 10 rad/s | 13 | 37 | 0.43 | — | 7.5 |
| G" 1 rad/s | 6.3 | 16 | 0.40 | — | 4.7 |
| 10 rad/s | 11 | 21 | 2.2 | — | 4.0 |
| tan δ 1 rad/s | 0.21 | 1.1 | 2.6 | — | 0.82 |
| 10 rad/s | 0.29 | 0.55 | 5.2 | — | 0.58 |

*Because of the nature of cross-linked silicone particles, measurements were impossible in Comparative Example 1.

Comparative Example 3

A cross-linkable silicone composition was prepared by mixing 94 parts by weight of a dimethylpolysiloxane having 400 mPa.s viscosity and dimethylvinyl and siloxy groups on both molecular terminals, and 6 parts by weight of a 30 mPa.s viscosity copolymer of methylhydridosiloxane and trimethylsiloxy groups on both molecular terminals with a content of silicon-bonded hydrogen atoms of 0.5 wt. %. The mixture was then combined with 53 parts by weight of a 3 wt. % aqueous solution of polyoxyethylene nonylphenylether (HLB =13.1). The mixture was emulsified and combined with 50 parts by weight of pure water. An aqueous emulsion of a cross-linkable silicone composition was produced.

The aforementioned aqueous emulsion of the cross-linkable silicone composition was uniformly mixed with a separately prepared aqueous emulsion of a platinum-type catalyst having 1,1 -divinyl-1,1,3,3-tetramethoxydisoloxane complex of platinum as its main component with an average particle diameter of the platinum-type catalyst equal to 0.05 μm; and a concentration of metallic platinum of 0.05 wt. %, so that the amount of metallic platinum in the aforementioned platinum catalyst in terms of weight units became equal to 20 ppm, compared to the amount of the dimethylpolysiloxane used in the emulsion which had dimethylvinylsiloxy groups on both molecular terminals. An aqueous emulsion of the cross-linkable silicone composition was prepared.

The obtained emulsion was kept intact at room temperature for one day, and then the cross-linkable silicone composition was subjected to a hydrosylilation reaction, whereby an aqueous suspension of cross-linked silicone particles having cross-linked silicone particles dispersed in drops of silicone oil in water was prepared. The suspension was combined with a 100 mPa.s viscosity emulsion of a 50 wt. % concentration of a dimethylpolysiloxane having trimethylsiloxy groups on both molecular terminals, so that the amount of the cross-linked silicone particles was increased four times. The mixture was then transferred to a 5 cm diameter aluminum plate, and water was removed from the emulsion by drying in air, while maintaining it in air draft for 3 days. As a result, a silicone composition consisting of a silicone oil and silicone particles was prepared. This silicone composition had a cream-like form, but the silicone oil was observed floating on the surface of the liquid. Observation of the composition under a stereoscopic microscope showed that cross-linked silicone particles were dispersed in the silicone oil non-uniformly. The cross-linked silicone particles were spherical in shape.

The invention is efficient in that it provides a silicone oil emulsion which contains cross-linked silicone particles in silicone oil drops which are dispersed in water, a method for the preparation of the aforementioned emulsion, and a method for the preparation a silicone composition with cross-linked silicone particles uniformly dispersed in a silicone oil.

Thus, there is provided herein a silicone oil emulsion comprising cross-linked silicone particles which have an average particle diameter of 0.1 to 100 μm and which are contained in silicone oil drops having an average diameter of 0.5 to 500 μm. The drops are dispersed in water, and the diameter of the cross-linked silicone particles is smaller than the diameter of the silicone oil drops. Also provided is a method for preparation of a silicone oil emulsion that contains cross-linked silicone particles of an average particle diameter from 0.1 to 100 μm in silicone oil drops of an average drop diameter from 0.5 to 500 μm, where the diameter of the cross-linked silicone particles is smaller than the diameter of the silicone oil drops. The method is characterized by the fact that a cross-linking reaction is caused by dispersing in water a cross-linkable silicone composition that contains a non-cross-linkable silicone oil. The contents of the non-cross-linkable silicone oil exceed the contents of the non-cross-linkable silicone oil in the product of cross-linking of the cross-linkable silicone composition. Lastly, there is provided a method for the preparation of a silicone composition comprising particles with an average diameter of 0.1 to 100 μm that are dispersed in a silicone oil. This method is characterized by removing water from a silicone oil emulsion which contains the cross-linked silicone particles having an average particle diameter of 0.1 to 100 μm. The particles are contained in silicon oil drops having an average diameter of 0.5 to 500 μm and are dispersed in water. The diameter of the cross-linked silicone particles is smaller than the diameter of the silicone oil drops.

Other variations may be made in compounds, compositions, and methods described herein without departing from the essential features of the invention. The embodiments of the invention specifically illustrated herein are exemplary only and not intended as limitations on their scope except as defined in the appended claims.

We claim:

1. A silicone oil emulsion comprising cross-linked silicone particles which have an average particle diameter of 0.1 to 100 μm, the crosslinked silicone particles being contained in silicone oil drops having an average diameter of 0.5 to 500 μm, the silicone oil drops containing the cross-linked silicone particles being dispersed in water, the diameter of the cross-linked silicone particles being smaller than the diameter of the silicone oil drops, the cross-linked silicone particles being prepared by a hydrosilylation cross-linking reaction or a condensation cross-linking reaction between (i) an organopolysiloxane having in its molecule at least two alkenyl groups and an organopolysiloxane having in its molecule at least two silicone-bonded hydrogen atoms, or (ii) an organopolysiloxane which contains a hydrolyzable group and a silane-type cross-linking agent having a hydrolyzable group, respectively.

2. The silicone oil emulsion of claim 1 wherein the silicone oil has a viscosity of 1 to 100,000,000 mPa.s.

3. A method of manufacturing a silicone oil emulsion containing cross-linked silicone particles of an average particle diameter of 0.1 to 100 μm in silicone oil drops of an average drop diameter of 0.5 to 500 μm and wherein the diameter of the cross-linked silicone particles is smaller than the diameter of the silicone oil drops, the method comprising dispersing in water a cross-linkable silicone composition, the cross-linkable composition containing a non-cross-linkable silicone oil in an amount which exceeds the amount of non-cross-linkable silicone oil which can be held by the product of crosslinking of the cross-linkable silicone composition, the cross-linked silicone particles being prepared by a hydrosilylation cross-linking reaction or a condensation cross-linking reaction between (i) an organopolysiloxane having in its molecule at least two alkenyl groups and an organopolysiloxane having in its molecule at least two silicone-bonded hydrogen atoms, or (ii) an organopolysiloxane which contains a hydrolyzable group and a silane-type cross-linking agent having a hydrolyzable group, respectively.

4. The method of manufacturing a silicone oil emulsion according to claim 3 wherein the non-cross-linkable silicone oil has a viscosity of 1 to 100,000,000 mPa.s.

5. A method for the preparation of a silicone composition containing cross-linked silicone particles with an average diameter of 0.1 to 100 μm which are dispersed in a silicone oil, the method comprising removing water from a silicone oil emulsion which contains the cross-linked silicone particles, the particles being contained in silicone oil drops of an average diameter of 0.5 to 500 μm, the silicone oil drops containing the cross-linked silicone particles being dispersed in the water, the diameter of the cross-linked silicone particles being smaller than the diameter of the silicone oil drops, the cross-linked silicone particles being prepared by a hydrosilylation cross-linking reaction or a condensation cross-linking reaction between (i) an organopolysiloxane having in its molecule at least two alkenyl groups and an organopolysiloxane having in its molecule at least two silicone-bonded hydrogen atoms, or (ii) an organopolysiloxane which contains a hydrolyzable group and a silane-type cross-linking agent having a hydrolyzable group, respectively.

6. The method for the preparation of a silicone composition according to claim 5 wherein the silicone oil has a viscosity of 1 to 100,000,000 mPa.s.

* * * * *